(12) United States Patent
Platt et al.

(10) Patent No.: US 6,489,896 B1
(45) Date of Patent: Dec. 3, 2002

(54) AIR IN-LINE SENSOR FOR AMBULATORY DRUG INFUSION PUMP

(75) Inventors: Michael Platt, Mt. Prospect, IL (US); Ralph LaBedz, McHenry, IL (US); Patrick Hovis, Rockford, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/706,371

(22) Filed: Nov. 3, 2000

(51) Int. Cl.[7] ............................................. G08B 17/00
(52) U.S. Cl. ..................... 340/632; 340/621; 340/603
(58) Field of Search ................................. 340/603, 621, 340/632; 604/122, 123; 128/DIG. 13; 73/19.1

(56) References Cited

U.S. PATENT DOCUMENTS

| | | | | |
|---|---|---|---|---|
| 4,764,166 A | * | 8/1988 | Spani | 604/65 |
| 4,821,558 A | * | 4/1989 | Pastrone et al. | 73/19 |
| 4,981,467 A | | 1/1991 | Bobo, Jr. et al. | 604/65 |
| 5,102,392 A | | 4/1992 | Sakai et al. | 604/122 |
| 5,123,275 A | * | 6/1992 | Daoud et al. | 73/19.3 |
| 5,177,993 A | * | 1/1993 | Beckman et al. | 73/19.03 |
| 5,537,853 A | * | 7/1996 | Fingurgh et al. | 73/19.3 |

* cited by examiner

*Primary Examiner*—Julie Lieu
(74) *Attorney, Agent, or Firm*—Paul J. Nykaza; Wallenstein & Wagner Ltd.

(57) ABSTRACT

An air in-line sensor for detecting air bubbles in a therapeutic solution flowing through a tube utilizes a unitary type sensor having a channel for receiving the tube. The channel has a tube loading section. A signal emitting member is positioned on one side of the tube and a signal receiving member is positioned on an opposite side of the tube. A first air baffle is positioned between the signal emitting and signal receiving members.

34 Claims, 3 Drawing Sheets

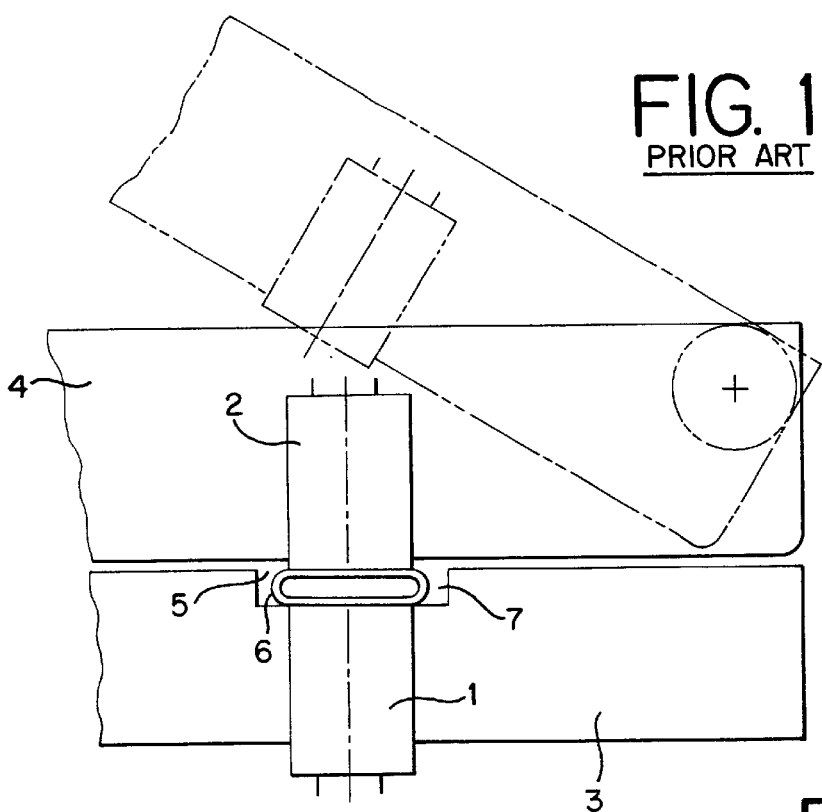
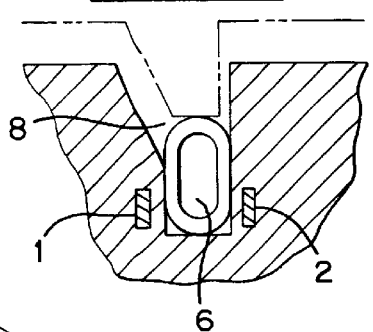
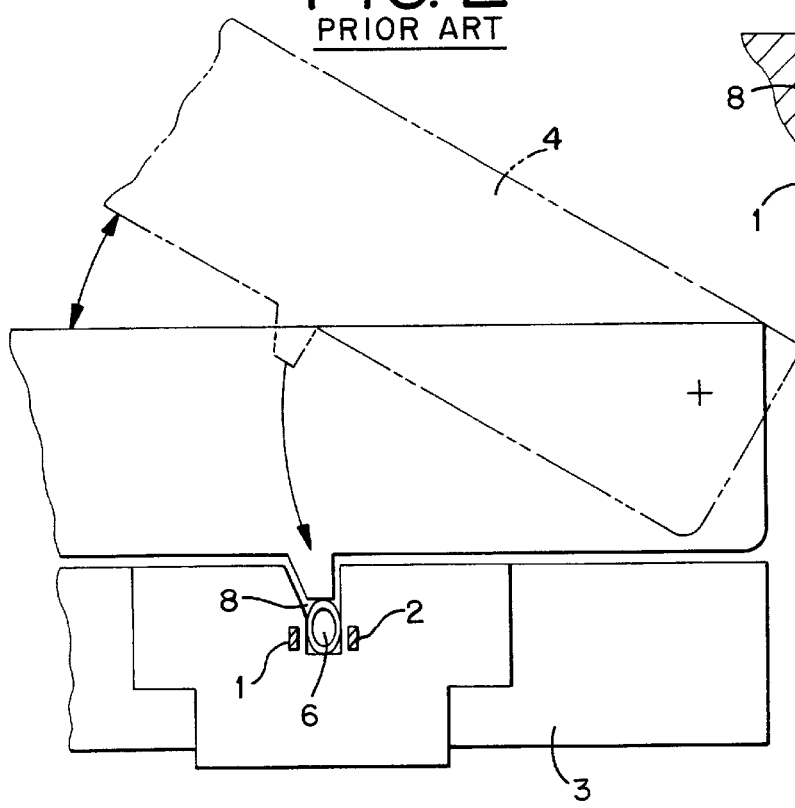

AIR IN-LINE SENSOR FOR AMBULATORY DRUG INFUSION PUMP

TECHNICAL FIELD

The present invention relates to an air in-line sensor for use in a medical device and, more particularly, to an air in-line sensor designed to detect air bubbles in a therapeutic solution flowing through a tube.

BACKGROUND OF THE INVENTION

An infusion system for delivering a drug or other liquid into a patient often includes an infusion device that operates to deliver the liquid at an adjustable rate or dosage. Prior art infusion devices include an air detector using an ultrasonic or an optical sensor for detecting air bubbles in the liquid flowing through a tube. The air detector is loaded in a part of the tube.

Two types of the air detectors are known. More specifically, in the separate type as shown in FIG. 1, a signal emitting member 1 and a signal receiving member 2 of the detector are separate components in such a structure. The signal emitting member 1 is mounted on a stationary unit 3 of a pumping station, while the signal receiving member 2 is carried by a movable unit 4, such as a door. When the door 4 is closed, a channel 5 is defined between an upper surface of signal emitting member 1 of stationary unit 3 and a lower surface of signal receiving member 2 of movable unit 4, into which a tube 6 is accommodated. Accordingly, when movable unit 4 is closed while tube 6 is loaded into an upper recess 7 defined in signal emitting member 1 of stationary unit 3, tube 6 is deformed into a flattened configuration within channel 6 to provide an enlarged surface area in contact with signal emitting and receiving members 1 and 2. receiving members 1 and 2 are embedded in opposing walls of groove 8. The unitary type is mainly used for detecting relatively short air bubbles and therefore the length of tube-receiving groove 8 is relatively short, exerting less resistance in contact between the groove and the tube. Accordingly, the tube may be fitted into groove 8 by pushing with one's fingers.

In the above-described separate type, it is difficult to maintain a constant, specific distance between the signal emitting and receiving members so as to stabilize the performance of the detector, because the separate type sensor system has more tolerances than a unitary type system. When more tolerances are involved, distance control between the signal emitting and receiving members becomes more difficult.

Nuisance alarms result when a pump alarm is activated when air is not present in the line. As a result, air sensors are often deactivated in the pump's configuration. Accordingly, the pump would not be able to detect the presence of air in the line. Moreover, nondetection of actual air in the tubing line occurs in many prior art infusion devices because the ultrasonic signal is not fully transmitted through the tube. For example, an ultrasonic signal may work its way around the bottom of the channel and trick the pump mechanism into believing that liquid is in the line when, in fact, air is in the line. This nondetection or "short circuit" is undesirable.

Some unitary type air sensors have included a pocket underneath the channel to block the ultrasonic signal, and thus, prevent the ultrasonic signal from circumventing the correct path through the tubing set. However, these pockets can allow dirt and cleaning solutions to build up, which prevents the sensor from working properly. If the pocket became filled with liquid, the ultrasonic signal may travel around the channel even when air is present in the tubing line.

Moreover, some unitary type air sensor systems do not maintain optimal contact between the tube and the channel. For example, if a flat closure member surface is utilized to push the tube into a V-shaped, upper section of the channel, the tube may become dislodged from the channel by rotational or rolling displacement of the tube. Additionally, the tube may flatten or collapse disproportionately, causing poor coupling between the tube and the channel.

U.S. Pat. No. 5,102,392, owned by Assignee of the present invention, discloses an air detector for use in infusion pumps (see FIGS. 2 and 3). The air detector utilizes a unitary type sensor for detecting air bubbles in the tube. The upper section of the groove has a first side wall which tapers upwardly and outwardly from the tube fixing section and a second side wall is perpendicular to the base of the groove along the length of the tube fixing section. When the door is closed after the tube is loaded in the groove, the tube abutting member forces the tube against the second side wall and into final position.

The present invention is provided to solve these and other problems.

SUMMARY OF THE INVENTION

The present invention provides an air in-line sensor for detecting air bubbles in a therapeutic solution flowing through a tube.

According to one aspect of the present invention, the sensor has a channel for receiving the tube having a tube loading section. The sensor further has a signal emitting member positioned on one side of the tube and a signal receiving member positioned on an opposite side of the tube. A first air baffle is positioned between the signal emitting member and the signal receiving member.

According to another aspect of the invention, the sensor has a first lead-in section defined by an upper portion of a first sidewall of the channel. The first lead-in section tapers upwardly and outwardly from an intermediate portion of the first sidewall to the upper portion of the first sidewall.

According to a further aspect of the invention, the sensor has a second lead-in section positioned opposite the first lead-in section. The second lead-in section is defined by an upper portion of a second sidewall of the channel, and the second lead-in section tapers upwardly and outwardly from an intermediate portion of the second sidewall to the upper portion of the second sidewall.

According to a further aspect of the invention, the sensor has a second air baffle positioned between the signal emitting and the signal receiving members.

According to yet another aspect of the invention, an air in-line sensor is provided for detecting air bubbles in a therapeutic solution flowing through a tube. The sensor has a channel for receiving the tube having a tube loading section. Preferably, the tube has a first lead-in section. The tube loader has a stationary section and a movable section hingedly connected to the stationary section. The movable section has a blade having a radius of curvature for positioning the tube in the tube loading section. Preferably, a signal emitting member is positioned on one side of the tube and a signal receiving member is positioned on an opposite side of the tube.

According to a further aspect of the invention, an air in-line sensor system is disclosed for detecting air bubbles in a therapeutic solution flowing through a tube located in a pumping mechanism. The tube extends from a supply bag of the therapeutic solution to a patient through the system. The system has a channel for receiving the tube having a first lead-in section, and a tube loading section. A signal emitting member is positioned on one side of the tube and a signal receiving member is positioned on an opposite side of the tube. A first air baffle is positioned between the signal emitting member and the signal receiving member. Moreover, the tube loader has a stationary section and a movable section hingedly connected to the stationary section. The movable section has a blade having a radius of curvature for positioning the tube in the tube loading section.

According to yet another aspect of the invention, a method is disclosed for loading a tube into a channel of a medical pump. Preferably, the channel is provided having a first lead-in section and a tube loading section. The channel is also provided having a signal emitting member positioned on one side of the tube and a signal receiving member positioned on an opposite side of the tube. A tube loader is provided having a stationary section and a movable section. The movable section has a blade having a radius of curvature. The tube is positioned proximate the channel. The blade is placed in contact with the tube, and the blade is then moved until the tube is positioned within the tube loading section.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 1 is a schematic front elevational view of a prior art air in-line sensor of the separate type;

FIG. 2 is a schematic front elevational view of a prior art air in-line sensor of the unitary type;

FIG. 3 is cross-sectional view of the prior art air in-line sensor of FIG. 2, showing the loading process of a tube;

DETAILED DESCRIPTION OF THE PREFERRED EMBODIMENT

Figure 4:
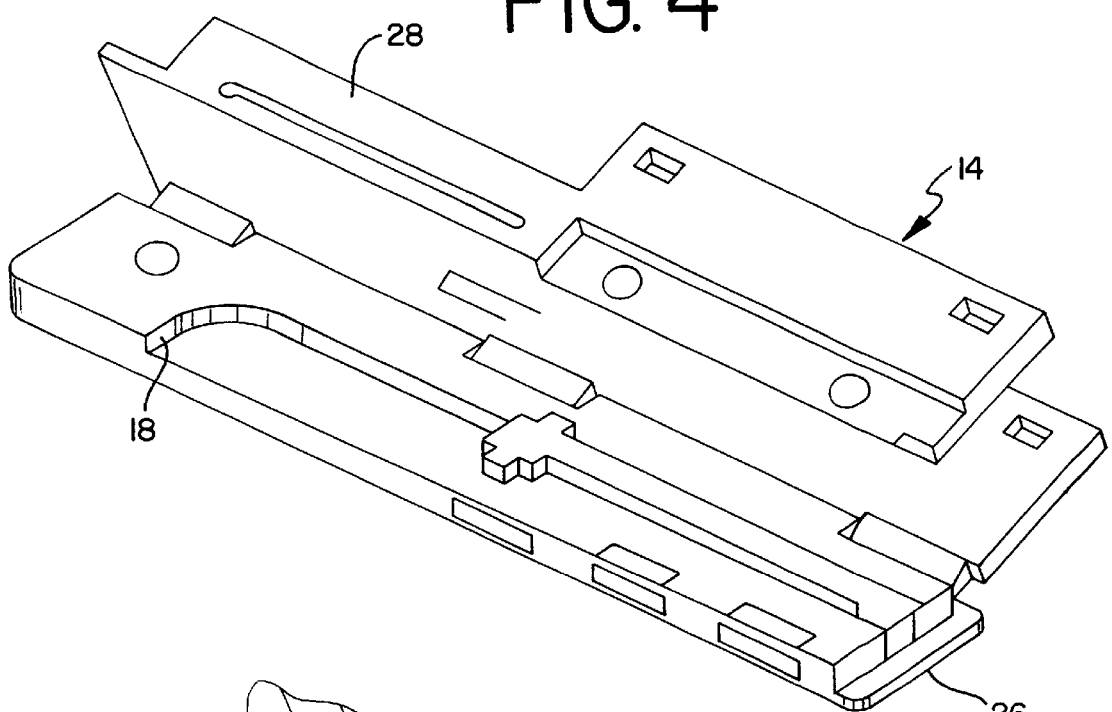
FIG. 4 is a perspective view of a tube loader according to a preferred aspect of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Figure 5:
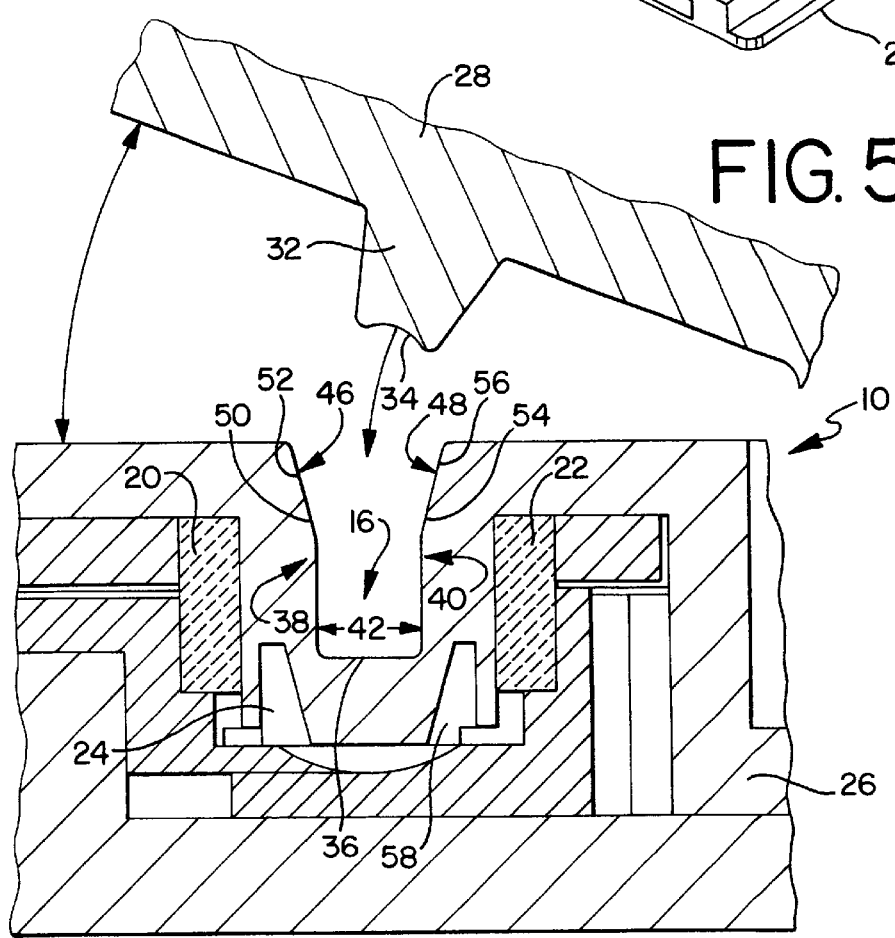
FIG. 5 is a schematic front elevational view of an air in-line sensor according to a preferred aspect of the present invention.
Figure 6:
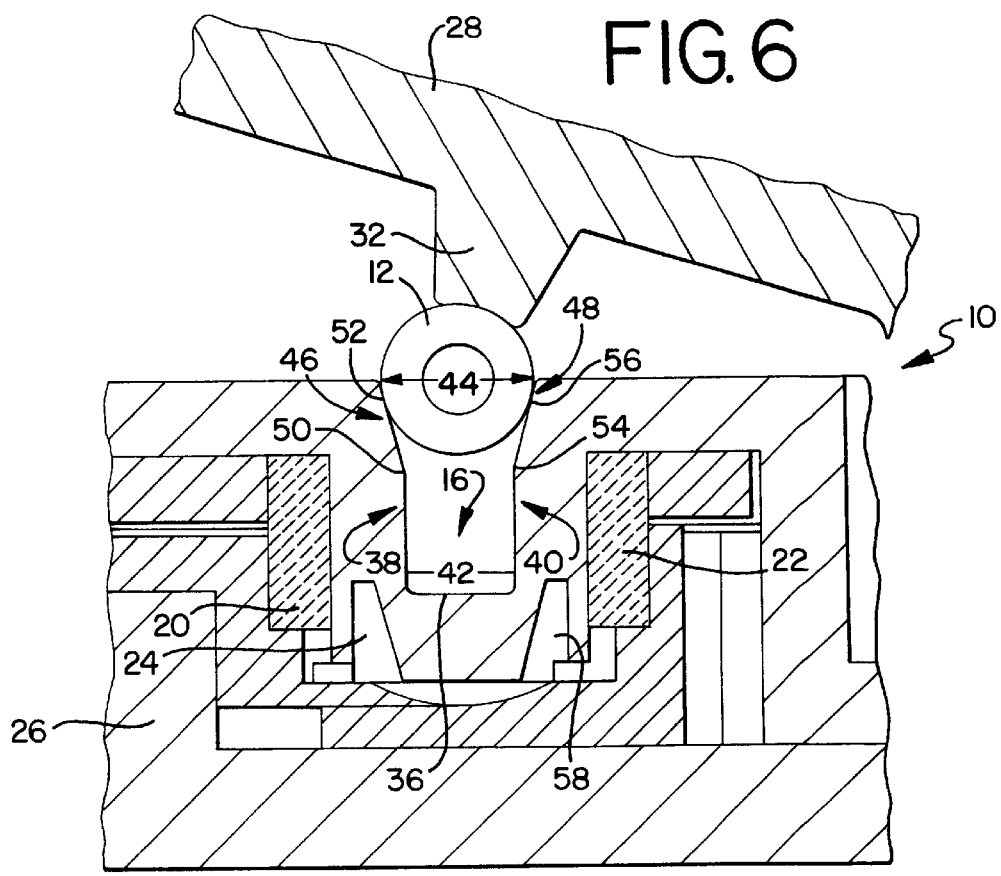
FIG. 6 is a cross-sectional view of the air in-line sensor of FIG. 5, showing the loading process of a tube.
Figure 7:
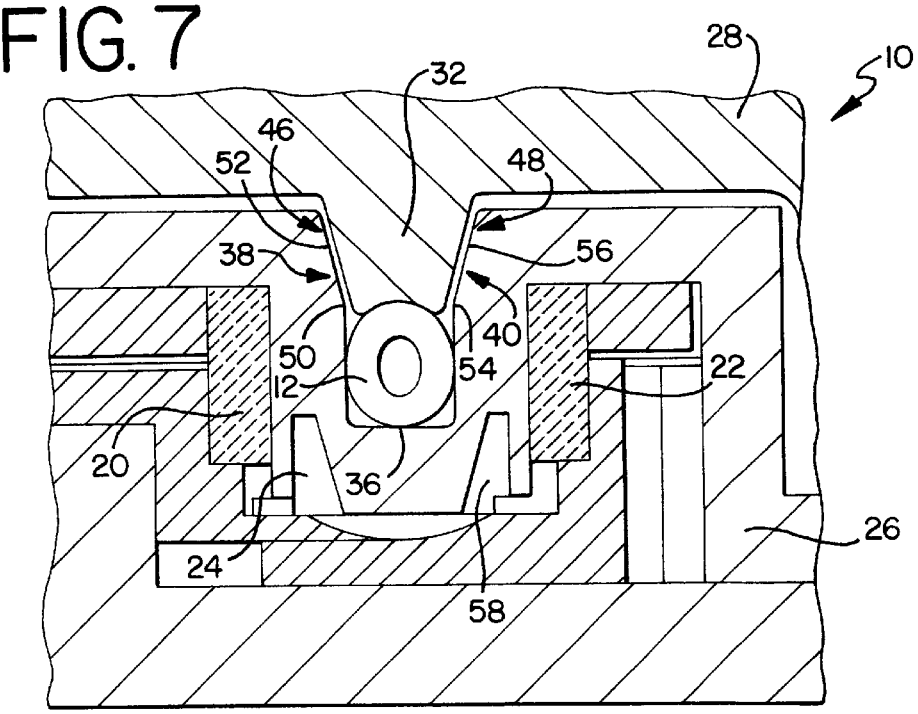
FIG. 7 is another cross-sectional view of the air in-line sensor of FIG. 5, showing the loading process of a tube.

Referring now in detail to the Figures, FIGS. 5–7 illustrate an air in-line sensor 10 for detecting air bubbles in a therapeutic solution flowing through a tube 12 located in a pumping mechanism 14 (see FIG. 4). Tube 12 extends from a supply bag of the therapeutic solution to a patient through sensor 10. Sensor 10 has a channel 16 for receiving tube 12 and a tube loading section 18. Sensor 10 also has a signal emitting member 20 positioned on one side of tube 12 and a signal receiving member 22 positioned on an opposite side of tube 12. Further, sensor 10 has a first air baffle 24 positioned between signal emitting member 20 and signal receiving member 22 to prevent the ultrasonic signal from traveling around tube 12.

Preferably, pumping mechanism 14 is a peristaltic pump, a roller pump, an expulsor pump, a finger pump or a piston cassette pump. Pumping mechanism 14 has a stationary section 26 and a movable section 28 hingedly connected to stationary section 26. As shown in FIG. 5, movable section 28 is pivotable about its axis in a direction indicated by an arrow to close and open stationary section 26.

Movable section 28 has a blade 32 having a radius of curvature 34 for positioning tube 12 in pumping mechanism 14. Blade 32 pushes tube 12 into the proper position within channel 16. In a preferred aspect of the invention, channel 16 is U-shaped, and has substantially square corners having only a slight radius where base 36 meets first and second sidewalls 38 and 40, respectively. As shown in FIG. 6, the width 42 of channel 16 is smaller than outer diameter 44 of tube 12. This provides a large contact area between tube 12 and first and second sidewalls 38 and 40, respectively.

Channel 16 has a first lead-in section 46 and a second lead-in section 48 to allow tube 12 to be easily loaded into pumping mechanism 14. Each of the first and second lead-in sections 46 and 48, respectively, includes a V-radius and a channel draft for molding purposes. Channel 16 has a first lead-in section 46 forming the upper portion of a first sidewall 38 of channel 16. First lead-in section 46 tapers upwardly and outwardly from an intermediate portion 50 of first sidewall 38 to upper portion 52 of first sidewall 38.

In a preferred aspect of the invention, channel 16 has a second lead-in section 48 positioned opposite first lead-in section 46. Second lead-in section 48 forms the upper portion of a second sidewall 40 of channel 16. Similar to first lead-in section 46, second lead-in section 48 tapers upwardly and outwardly from an intermediate portion 54 of second sidewall 40 to the upper portion 56 of second sidewall 40.

As shown in FIGS. 6 and 7, blade 32 has a radius of curvature substantially identical to the radius of curvature of tube 12 to maximize coupling of tube 12 and first and second sidewalls 38 and 40 of channel 16. The curved blade allows tube 12 to be pushed down into channel 16 with a maximum amount of force imparted on first and second sidewalls 38 and 40, respectively, without distorting tube 12. The pressure exerted on tube 12 causes the sides of tube 12 to expand horizontally and push against first and second sidewalls 38 and 40, respectively. Thus, tube 12 is deformed from a circular configuration into an oval configuration.

The greater the force of the sides of tube 12 on first and second sidewalls 38 and 40, respectively, and the greater the contact area of tube 12 and first and second sidewalls 38 and 40, the greater the coupling between tube 12 and channel 16, and thus, the greater the transmission of the ultrasonic signal through tube 12. The higher coupling force increases the performance of air sensor 10.

An electronic circuit drives signal emitting member 20 which projects ultrasonic energy across channel 16, tube 12 and the tube contents. Signal receiving member 22 acts as a receiver. The strength of the ultrasonic signal passing through tube 12 is highest when liquid is present in tube 12. Conversely, the strength of the ultrasonic signal is lowest when air is present in tube 12. The electrical circuit compares the strength of the detected signal and decides whether there is air or liquid in tube 12, and thus, whether to sound an air in-line alarm. When air passes through tube 12, and thus, the transmission path, the ultrasonic energy is interrupted or decreased. Accordingly, the electrical circuit will output five(5) volts if liquid is present in tube 12, and the electrical circuit will output zero(0) volts if air is present in tube 12.

In a preferred aspect of the invention, sensor 10 has a second air baffle 58 positioned between signal emitting member 20 and signal receiving member 22. Second air baffle 58 is positioned opposite first air baffle 24, which prevents the ultrasonic signal from traveling around tube 12. First air baffle 24 weakens the ultrasonic signal traveling through tube 12, and thus, prevents a "short circuit" when high coupling forces are present between tube 12 and first and second sidewalls 38 and 40 and base 36.

As shown in FIG. 7, the center of signal emitting and receiving members 20 and 22 and the center of tube 12 are co-linear and parallel to channel 16 when tube 12 is positioned within channel 16. Channel 16 is dimensioned to allow these respective centers to align when tube 12 is forced into channel 16 and to reduce manufacturing error. Proper align increases the strength of the signal transmitted through tube 12.

The width of channel 16 is selected in conjunction with the dimensions of tube 12 to optimize the performance of air sensor 10. Preferably, channel 16 is made of an engineering resin, such as ABS plastic, and has a width of about 0.075 inches at its base. Preferably, the outer diameter of tube 12 is about 0.083 inches, and the inner diameter is 0.03 inches. The thickness of the U-channel material between tube 12 and the signal emitting and signal receiving members 20 and 22, respectively, is critical, and, preferably, is 0.027 inches. The U-channel wall surface finish was also optimized to increase the coupling between the tubing set and the plastic U-channel walls. Preferably, the U-channel wall is made of a continuous plastic that is free of voids, glass and fillers.

In another aspect of the invention, an air in-line sensor 10 is provided for detecting air bubbles in a therapeutic solution flowing through tube 12. Sensor 10 has means for emitting an ultrasonic signal through tube 12. Preferably, the means for emitting is a transducer, such as signal emitting member 20. Sensor 10 also has means for detecting the ultrasonic signal emitted through tube 12. Preferably, the means for detecting is a transducer, such as signal receiving member 22.

Sensor 10 further has means for preventing the ultrasonic signal from traveling around tube 10. Preferably, the means for preventing employs two air baffles, such as first air baffle 24 and second air baffle 58. Air baffles 24 and 58 are positioned between signal emitting member 20 and signal receiving member 22.

Sensor 10 also has means for measuring the strength of the ultrasonic signal emitted through tube 12. Preferably, the means for measuring is an electrical circuit. Moreover, sensor 10 has means for comparing the strength of the ultrasonic signal to a preset voltage value. Preferably, the means for comparing employs a voltage comparator.

Sensor 10 further has means for outputting a preset, maximum value if liquid is present in tube 12 and a preset, minimum value if air is present in tube 12. Preferably, the electrical circuit will output five (5) volts if liquid is present in tube 12, and the electrical circuit will output zero (0) volts if air is present in tube 12. For example, the voltage comparator is set at 2.5 volts. A signal above 2.5 volts would cause the comparator to output 5 volts, and thus, indicate that liquid is present in tube 12. Conversely, a signal below 2.5 volts would cause the comparator to output 0 volts, and thus, indicate that air is present in tube 12. If air is present in tube 12, sensor 10 sounds an air in-line alarm.

A method is disclosed for loading tube 12 into channel 16. Preferably, channel 12 has first lead-in section 46 and tube loading section 18. Signal emitting member 20 is positioned on one side of tube 12 and signal receiving member 22 is positioned on an opposite side of tube 12. Pumping mechanism 14 is provided having stationary section 26 and movable section 28. Movable section 28 has blade 32 having radius of curvature 34. Tube 12 is positioned in channel 16, and blade 32 is placed in contact with tube 12. When movable section 28 is closed, blade 32 positions tube 12 in tube loading section 18.

While the specific embodiments have been illustrated and described, numerous modifications come to mind without significantly departing from the spirit of the invention, and the scope of protection is only limited by the scope of the accompanying Claims.

We claim:

1. An air in-line sensor for detecting air bubbles in a therapeutic solution flowing through a tube, the sensor comprising:

a channel for receiving the tube having a tube loading section;

a signal emitting member positioned on one side of the tube and a signal receiving member positioned on an opposite side of the tube; and, a first air baffle positioned between the signal emitting member and the signal receiving member.

2. The sensor of claim 1 further comprising a first lead-in section.

3. The sensor of claim 2 wherein the first lead-in section comprises an upper portion of a first sidewall of the channel, the first lead-in section tapers upwardly and outwardly from an intermediate portion of the first sidewall to the upper portion of the first sidewall.

4. The sensor of claim 1 wherein the first air baffle prevents an ultrasonic signal from traveling around the tube.

5. The sensor of claim 1 further comprising a second air baffle.

6. The sensor of claim 5 wherein the second air baffle is positioned between the signal emitting member and the signal receiving member.

7. The sensor of claim 6 wherein the second air baffle prevents an ultrasonic signal from traveling around the tube.

8. The sensor of claim 1 further comprising a second lead-in section positioned opposite the first lead-in section.

9. The sensor of claim 8 wherein the second lead-in section comprises an upper portion of a second sidewall of the channel, the second lead-in section tapers upwardly and outwardly from an intermediate portion of the second sidewall to the upper portion of the second sidewall.

10. An air in-line sensor for detecting air bubbles in a therapeutic solution flowing through a tube, the sensor comprising:

a channel for receiving the tube having a first lead-in section, and a tube loading section;

a signal emitting member positioned on one side of the tube and a signal receiving member positioned on an opposite side of the tube; and, a first air baffle positioned between the signal emitting member and the signal receiving member.

11. The sensor of claim 10 wherein the first lead-in section comprises an upper portion of a first sidewall of the channel, the first lead-in section tapers upwardly and outwardly from an intermediate portion of the first sidewall to the upper portion of the first sidewall.

12. The sensor of claim 10 wherein the first air baffle prevents an ultrasonic signal from traveling around the tube.

13. The sensor of claim 10 further comprising a second air baffle.

14. The sensor of claim 13 wherein the second air baffle is positioned between the signal emitting member and the signal receiving member.

15. The sensor of claim 14 wherein the second air baffle prevents an ultrasonic signal from traveling around the tube.

16. The sensor of claim 10 further comprising a second lead-in section positioned opposite the first lead-in section.

17. The sensor of claim 16 wherein the second lead-in section comprises an upper portion of a second sidewall of the channel, the second lead-in section tapers upwardly and outwardly from an intermediate portion of the second sidewall to the upper portion of the second sidewall.

18. An air in-line sensor for detecting air bubbles in a therapeutic solution flowing through a tube, the sensor comprising:
    a channel for receiving the tube having a tube loading section;
    a first lead-in section comprising an upper portion of a first sidewall of the channel, the first lead-in section tapers upwardly and outwardly from an intermediate portion of the first sidewall to the upper portion of the first sidewall;
    a second lead-in section comprising an upper portion of a second sidewall of the channel, the second lead-in section tapers upwardly and outwardly from an intermediate portion of the second sidewall to the upper portion of the second sidewall; and,
    the tube loading section having a stationary section and a movable section hingedly connected to the stationary section, the movable section having a blade having a radius of curvature for positioning the tube in the tube loading section.

19. An air in-line sensor system for detecting air bubbles in a therapeutic solution flowing through a tube located in a pumping mechanism, the tube extending from a supply bag of the therapeutic solution to a patient through the system, the system comprising:
    a channel for receiving the tube having a first lead-in section, and a tube loading section;
    a signal emitting member positioned on one side of the tube and a signal receiving member positioned on an opposite side of the tube;
    a first air baffle positioned between the signal emitting member and the signal receiving member; and,
    the tube loader having a stationary section and a movable section hingedly connected to the stationary section, the movable section having a blade having a radius of curvature for positioning the tube in the tube loading section.

20. The system of claim 19 wherein the pumping mechanism is selected from the group consisting of a peristaltic pump, a roller pump, an expulsor pump, a finger pump and a piston cassette pump.

21. The sensor of claim 19 wherein the first lead-in section comprises an upper portion of a first sidewall of the channel, the first lead-in section tapers upwardly and outwardly from an intermediate portion of the first sidewall to the upper portion of the first sidewall.

22. The sensor of claim 19 wherein the first air baffle prevents an ultrasonic signal from traveling around the tube.

23. The sensor of claim 19 further comprising a second air baffle.

24. The sensor of claim 23 wherein the second air baffle is positioned between the signal emitting member and the signal receiving member.

25. The sensor of claim 24 wherein the second air baffle prevents an ultrasonic signal from traveling around the tube.

26. The sensor of claim 19 further comprising a second lead-in section positioned opposite the first lead-in section.

27. The sensor of claim 26 wherein the second lead-in section comprises an upper portion of a second sidewall of the channel, the second lead-in section tapers upwardly and outwardly from an intermediate portion of the second sidewall to the upper portion of the second sidewall.

28. An air in-line sensor for detecting air bubbles in a therapeutic solution flowing through a tube, the sensor comprising:
    means for emitting an ultrasonic signal through the tube;
    means for preventing the ultrasonic signal from traveling around the tube;
    means for detecting the ultrasonic signal emitted through the tube;
    means for measuring the strength of the ultrasonic signal emitted through the tube;
    means for comparing the strength of the ultrasonic signal to a preset voltage value;
    means for outputting a preset, maximum value for liquid and a preset, minimum value for air; and,
    means for determining whether to sound an air in-line alarm.

29. The sensor of claim 28 wherein the means for emitting is a transducer.

30. The sensor of claim 28 wherein the means for preventing employs two air baffles positioned between a signal emitting member and a signal receiving member.

31. The sensor of claim 28 wherein the means for detecting is a transducer.

32. The sensor of claim 28 wherein the means for measuring employs an electrical circuit.

33. The sensor of claim 28 wherein the means for comparing employs a voltage comparator.

34. An air in-line sensor for detecting air bubbles in a therapeutic solution flowing through a tube, the sensor comprising:
    a channel for receiving the tube having a tube loading section;
    a signal emitting member positioned on one side of the tube and a signal receiving member positioned on an opposite side of the tube;
    a first lead-in section comprising an upper portion of a first sidewall of the channel, the first lead-in section tapers upwardly and outwardly from an intermediate portion of the first sidewall to the upper portion of the first sidewall; and,
    a second lead-in section comprising an upper portion of a second sidewall of the channel, the second lead-in section tapers upwardly and outwardly from an intermediated portion of the second sidewall to the upper portion of the second sidewall.

* * * * *